United States Patent [19]

Lennon

[11] Patent Number: 4,857,044
[45] Date of Patent: Aug. 15, 1989

[54] COMPACT TAMPON APPLICATOR WITH HOLLOW TAMPON AND RADIALLY EXPANDABLE APPLICATOR TUBE

[75] Inventor: Patrick G. Lennon, Neenah, Wis.
[73] Assignee: Kimberly-Clark Corporation, Neenah, Wis.
[21] Appl. No.: 134,425
[22] Filed: Dec. 17, 1987
[51] Int. Cl.$^4$ ............................................. A61F 13/20
[52] U.S. Cl. ...................................... 604/14; 604/16; 604/904
[58] Field of Search ...................... 604/11-18, 604/286, 904

[56] References Cited

U.S. PATENT DOCUMENTS

| | | | |
|---|---|---|---|
| 2,450,138 | 9/1948 | Harwood | 128/263 |
| 2,478,576 | 8/1949 | Fourness | 128/263 |
| 2,607,346 | 8/1952 | Milcent | 604/11 |
| 2,829,646 | 4/1958 | Kurkjian | 128/263 |
| 3,102,540 | 9/1963 | Bentov | 604/11 X |
| 3,351,060 | 11/1967 | DeWoskin | 604/11 |
| 4,010,751 | 3/1977 | Ring | 604/14 |
| 4,027,673 | 6/1977 | Poncy et al. | 604/904 X |
| 4,222,381 | 9/1980 | Widlund et al. | 604/904 X |
| 4,276,881 | 7/1981 | Lilaonitkul | 128/263 |

FOREIGN PATENT DOCUMENTS 527827 10/1940 United Kingdom ............... 604/15

*Primary Examiner*—Dalton L. Truluck
*Attorney, Agent, or Firm*—Paul L. Leipold; Thomas J. Connelly

[57] ABSTRACT

A compact tampon applicator is disclosed having a hollow first tube with a forward end and a rearward end. A tampon is slidably positioned within the first tube. The tampon has a longitudinally aligned central aperture formed therein which is open at both ends and has a withdrawal string attached thereto. The applicator also contains a radially expandable second tube having a forward end and a rearward end. The forward end is initially retained in the central aperture of the tampon and the rearward end initially extends out of the rearward end of the first tube. The second tube is capable of expanding radially once the forward end is removed from the tampon such that the second tube acquires a larger diameter and can be manually moved forward to eject the tampon from the first tube.

30 Claims, 4 Drawing Sheets

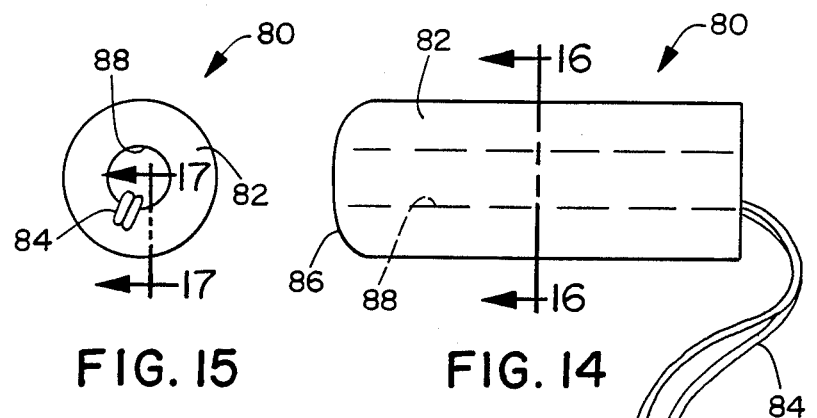
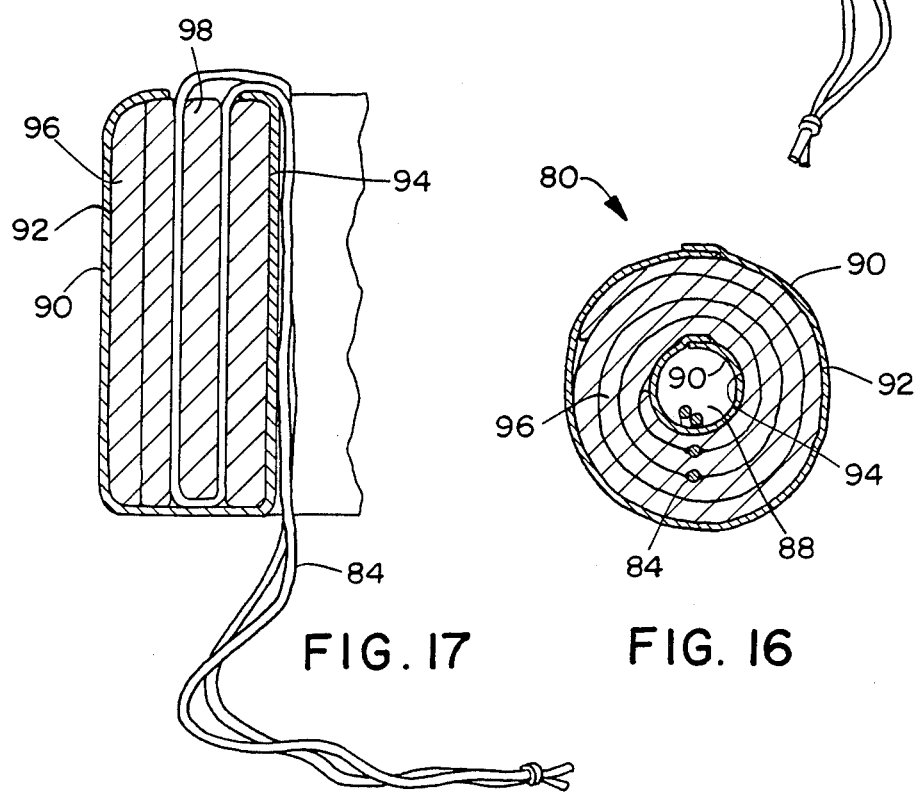

COMPACT TAMPON APPLICATOR WITH HOLLOW TAMPON AND RADIALLY EXPANDABLE APPLICATOR TUBE

FIELD OF THE INVENTION

This invention relates to a compact tampon applicator having a first tube, a tampon positioned in the first tube having an aperture formed therein and a radially expandable second tube. A portion of the second tube is initially retained within the aperture formed in the tampon such that when removed, the second tube will radially expand and can be used to eject the tampon from the first tube into a woman's vagina.

BACKGROUND OF THE INVENTION

Tampons represent one product for absorbing catamenial fluid which are used by many women because they are discreet and more portable than sanitary napkins. While tampons are only a couple of inches long, the traditional tube-type applicators add substantially to the length such that the combination may be four or more inches in length. The combination is so long that it cannot be easily carried by a woman in her hand without a portion of it being exposed.

Women prefer tampon applicators formed from molded plastic although many are still formed from rolled paper or cardboard. The plastic applicators include an outer tube containing a tampon or pledget, as it is sometimes referred to, and an inner tube which is designed to be pushed forward into the outer tube to eject the tampon into a woman's vagina. The formation and assembly of applicators with inner and outer tubes, including a mechanism to prevent the user from accidental disassembling the applicator by complete withdrawal of the inner tube, is difficult and expensive.

There are compact tampon applicators on the market today which are shorter than conventional applicators and which telescope prior to use so that initially they are only slightly longer than the tampon which is to be inserted. Various forms of such compact applicators are taught in U.S. Pats. Nos. 4,276,881 issued to Lilaonitkul, 3,101,713 issued to Sargent and 4,676,773 issued to Sheldon. However, these compact applicators are relatively complicated in design and expensive to fabricate.

There is currently a need for a compact tampon applicator which is discreet and can be easily carried by a woman in her hand or purse. Futhermore, there is a need for a compact tampon applicator which is economical, easy to manufacture and assemble and easy to use.

Most tampons are compressed or wound cylinders of fibrous material made from rayon, polyester or cotton. Other embodiments consist of bags of loose fibers or foam particles which are compressed into tampons. Regardless of the material used, there remains a problem with early leakage for the compression step hinders the ability of the tampon to initially expand and provide sufficient surface area for fluid absorption. Therefore, there is a need for a tampon that will be effective in stopping early leakage. This tampon must also be inexpensive and easy to manufacture.

SUMMARY OF THE INVENTION

Briefly, the present invention relates to a compact tampon applicator which retains a tampon which can be inserted into a woman's vagina. The compact tampon applicator comprises a hollow first tube having a forward end and a rearward end. A tampon is slidably positioned in the first tube. The tampon has a longitudinally aligned central aperture formed therein which is open at both ends and has a withdrawal string attached thereto. The applicator also includes a radially expandable second tube having a forward end and a rearward end. The forward end is initially retained in the central aperture of the tampon while the rearward end initially extends out of the rearward end of the first tube. The second tube is capable of radially expanding once the forward end is removed from the tampon such that the second tube acquires a larger diameter and can then be manually moved forward to eject the tampon from the first tube.

The general object of this invention is to provide a compact tampon applicator with a hollow tampon. A more specific object of this invention is to provide a compact tampon applicator having an outer tube, a hollow tampon positioned in the outer tube and a radially expandable inner tube initially retained in the hollow tampon.

Another object of this invention is to provide a discreet compact tampon applicator which contains a tampon which is effective in preventing leakage of menstrual fluid.

Still another object of the invention is to provide a low-cost, compact tampon applicator which is easy to manufacture and assemble.

Still further, an object of this invention is to provide a compact tampon applicator which utilizes a hollow tampon. Other objects and advantages of the present invention will become more apparent to those skilled in the art in view of the following description and accompanying drawings.

BRIEF DESCRIPTION OF THE DRAWINGS

FIG. 14 is a side view of a hollow tampon.

FIG. 15 is an end view of the tampon shown in FIG. 14.

FIG. 16 is a cross-sectional view of the tampon taken along line 16—16 of FIG. 14.

FIG. 17 is a cross-sectional view of the tampon taken along line 17—17 of FIG. 15.

DETAILED DESCRIPTION OF THE PREFERRED EMBODIMENTS

The compact tampon applicator of this invention has numerous advantages over conventional applicators. The hollow tampon is superior in leakage protection in that it presents a greater amount of surface area for absorption of menstrual fluids. The hollow tubular construction also permits easier handling during formation by automated equipment because the tampon can be centered and manipulated. The tampon design also facilitates insertion of the tampon into the plastic, outer tube of the compact tampon applicator.

The radially expandable inner tube is easily formed of relatively low-cost materials such as plastic sheets, paper tubes, and plastic tubes.

Figure 1:
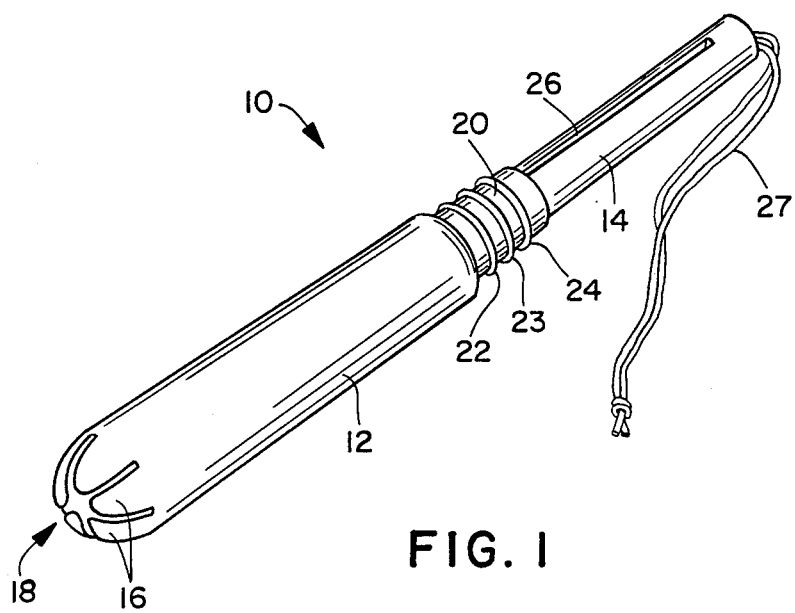
FIG. 1 is a perspective view of a compact tampon applicator shown in an extended condition.
Figure 2:
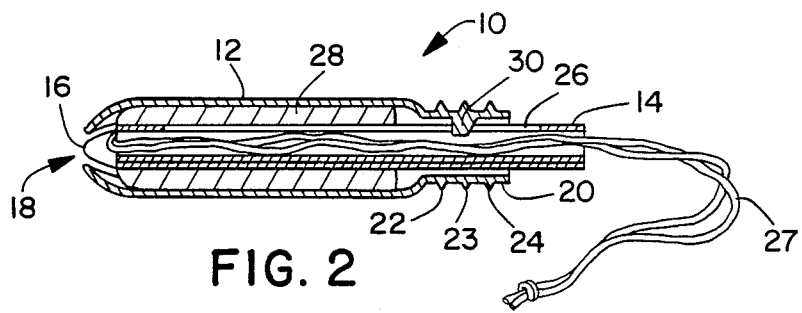
FIGS. 2, 3 and 4 are cross-sectional views of the compact tampon applicator shown in FIG. 1 depicting the initial position of the tampon and its movement as it is ejected from the outer tube by the inner tube.

Referring to FIGS. 1 and 2, a compact tampon applicator 10 is shown having an outer tube 12 and an inner tube 14. The outer tube 12 has a series of petals 16 formed at a forward end 18 which is designed to be inserted into a woman's vagina. The outer tube 12 is provided with a gripping portion 20 that includes ridges 22, 23 and 24. The inner tube 14 has an elongated slot 26 that aids in retaining the inner tube 14 in the outer tube 12. The cut-out slot 26 also aids in moving the inner tube 14 relative to the outer tube 12 during use. A withdrawal string 27 is attached to one end of a hollow tampon 28 and extends through the inner tube 14. The withdrawal string 27 is used to withdraw the tampon 28 from the vagina after use.

Figure 3:
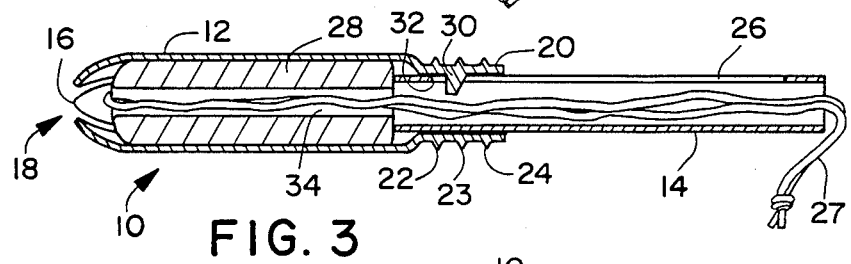

As illustrated in FIG. 2, the compact tampon applicator 10 is shown as it would be delivered to the ultimate user. The inner tube 14 is positioned within an aperture or opening 34 formed through the tampon 28 and extends to the forward end 18 of the outer tube 12. Preferably, the opening 34 extends longitudinally along the central axis of the tampon 28 and passes completely therethrough such that it is open at both ends. The gripping portion 20 has an inwardly extending projection 30 which engages the slot 26. When the tampon 28 is needed, the user withdraws the inner tube 14 from the tampon 28, as shown in FIG. 3, such that the slot 26 moves longitudinally with respect to the projection 30 and projection 30 contacts the forward end 32 of the slot 26. When the inner tube 14 is removed from the opening 34 formed in the hollow tampon 28, it will expand radially so as to acquire a larger diameter than the opening 34, see FIG. 4. The radial expansion of the inner tube 14 allows it to acquire a diameter that is larger than the diameter of the opening 34 but smaller than the outside diameter of the tampon 28. This size limitation permits the inner tube 14 to be used as the push mechanism to remove the tampon 28 out of the forward end 18 of the outer tube 12.

Figure 4:
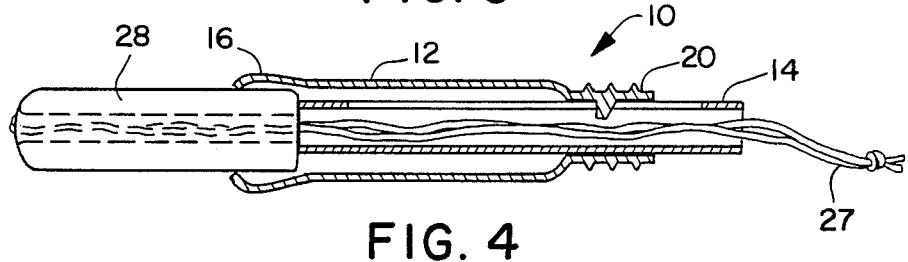

As illustrated in FIG. 4, the tampon 28 has been substantially ejected from the outer tube 12 by movement of the inner tube 14 forward. The tampon 28 is ejected from the outer tube 12 by movement of the inner tube 14 to the left and the outward displacement of the petals 16. The compact applicator 10 is then withdrawn from the vagina by the woman as she grips the gripping portion 20. The withdrawal string 27 will pass through the inner tube 14 and will remain with the tampon 28 for withdrawal of the tampon 28 after use.

Figure 5:
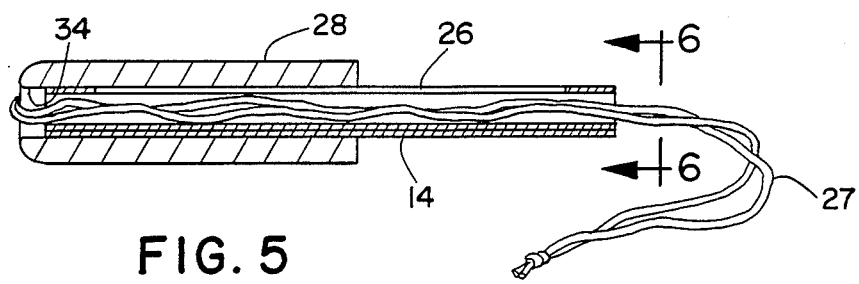
FIG. 5 is a cross-sectional view of a hollow tampon and the initial position of the inner tube within the hollow tampon.
Figure 7:
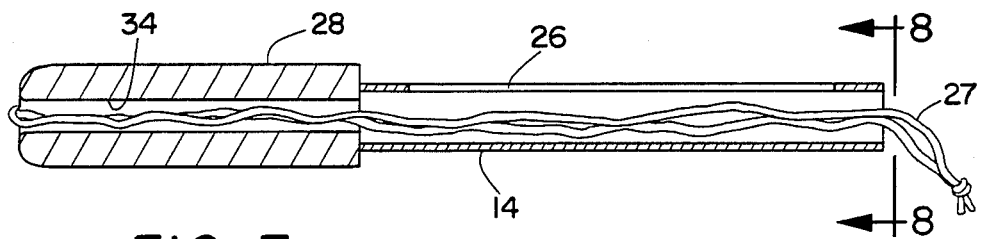
FIG. 7 is a cross-sectional view of a hollow tampon and an inner tube with the inner tube removed from the tampon and having expanded radially.
Figure 6:
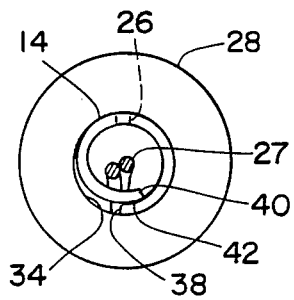
FIG. 6 is an end view of the tampon and inner tube taken along line 6—6 of FIG. 5.
Figure 8:
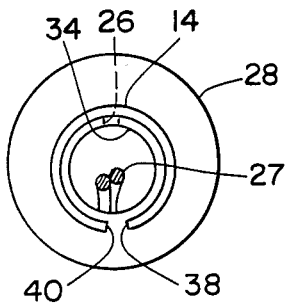
FIG. 8 is an end view of the tampon and inner tube taken along line 8—8 of FIG. 7.

Referring to FIGS. 5, 6, 7 and 8, the relationship of the inner tube 14 to the tampon 28 is shown. In FIG. 5, one end of the inner tube 14 is almost fully inserted in the opening 34 and the other end of the inner tube 14 is spaced away from the tampon 28. The withdrawal string 27 is attached to the forward end of the tampon 28 and is positioned in the inner tube 14 with the free end extending outward therefrom. The withdrawal string 27 should be longer than the length of both the tampon 28 and the inner tube 14 as is shown in FIG. 7. In FIG. 6, the inner tube 14 is shown having longitudinal edge 38 and 40 which have been overlapped at 42 to provide for a smaller diameter. After the inner tube 14 is withdrawn from the central opening 34 the inner tube 14 radially expands such that the edge 38 and 40 move apart and become opposed to each other thereby giving the inner tube 14 a larger diameter than the opening 34. This difference in diameter allows the forward motion of the inner tube 14 relative to the outer tube 12 to dislodge the tampon 28 from outer tube 12 and push it into a woman's vagina. As used herein, the forward end of the applicator 10 and the tampon 28 is the end that is inserted into the vagina first. The rearward end is the opposite end that extends outward from the woman's body during insertion.

Figure 9:
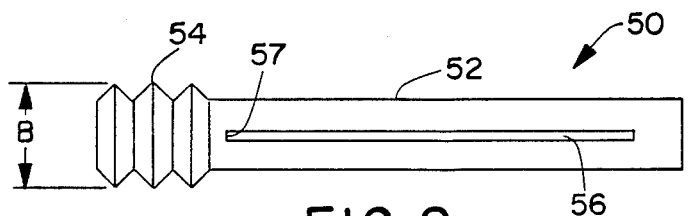
FIG. 9 is a side view of an alternate embodiment of an inner tube having pleats formed at one end.
Figure 10:
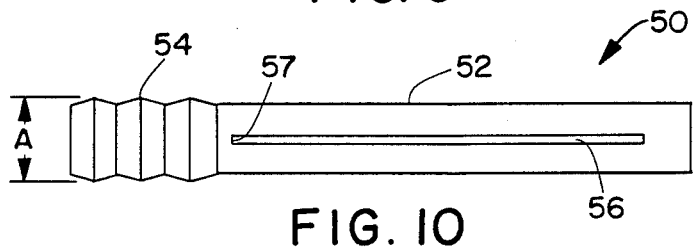
FIG. 10 is a side view of the inner tube shown in FIG. 9 depicting its shape while initially retained within a hollow tampon.

FIGS. 9 and 10 illustrate an alternative form of an inner tube, designated 50. The inner tube 50 has a generally cylindrical portion 52 and a pleated forward end 54. When the forward end 54 is stretched the pleats are removed and the diameter of the stretched portion 54, labeled A, is reduced to about the same diameter as the diameter of the cylindrical portion 52. In the relaxed condition, the pleated forward end 54 has a diameter labeled B, which is greater than the diameter of the trailing cylindrical portion 52. The inner tube 50 is also provided with a slot or groove 56 which has a forward end 57. The slot 56 is designed to cooperate with a projection formed on the outer tube 12 to limit the movement of the inner tube 50 and prevent it from rotating. The slot 56 also assures that the outer tube 12 and the inner tube 50 remain together while the forward end 57 determines the extent to which the inner tube 50 can be withdrawn from the outer tube 12.

Figure 11:
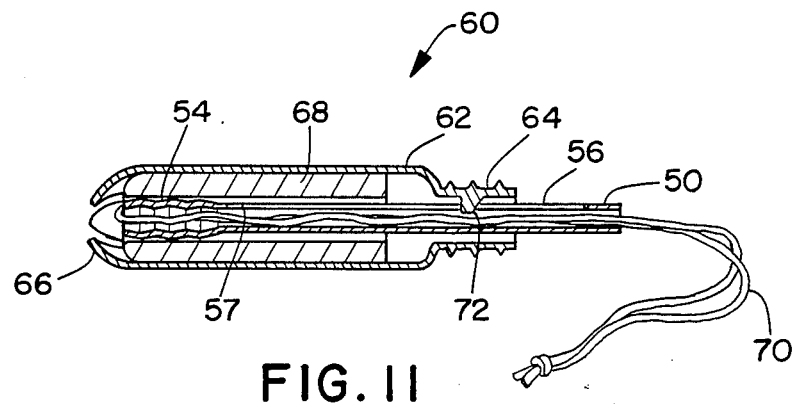
FIGS. 11, 12 and 13 are cross-sectional views of a compact tampon applicator depicting the initial position of the tampon and its movement as it is ejected from the outer tube by a pleated inner tube as shown in FIGS. 9 and 10.
Figure 12:
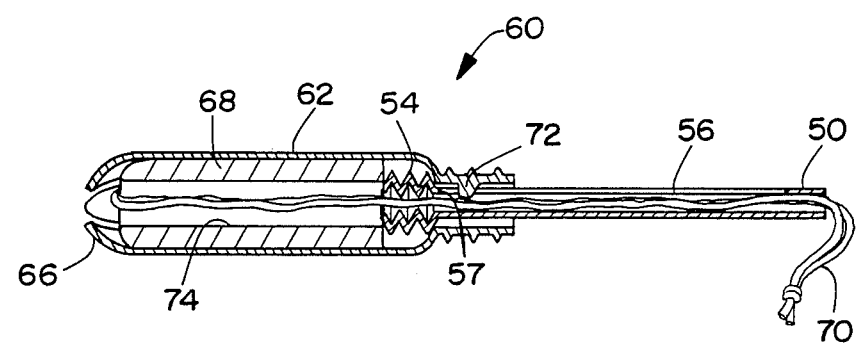
Figure 13:
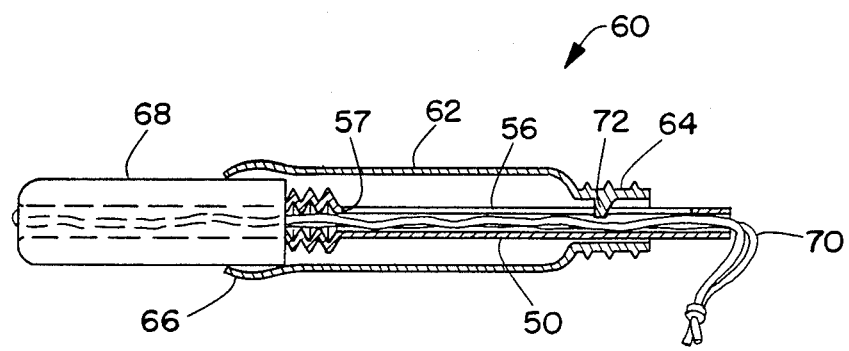

Referring to FIGS. 11, 12 and 13 a compact tampon applicator 60 is shown utilizing the inner tube 50. The compact applicator 60 includes the inner tube 50 and an outer tube 62. The outer tube 62 is provided with a finger grip portion 64 and has a forward petal shaped end 66. A cylindrical hollow tampon 68 having a longitudinal central aperture or opening 74 is positioned in the outer tube 62 and it is provided with a withdrawal string 70. The gripping portion 64 has a projection 72 formed on its interior diameter which cooperates with the slot 56 to prevent complete withdrawal of the inner tube 50 from the outer tube 62. As shown in FIG. 12, the inner tube 50 has been withdrawn from the cylindrical opening 74 formed in the tampon 68. The pleated section 54 expanded radially once it was withdrawn from the opening 74. Turning to FIG. 13, the inner tube 50 is shown being moved toward the forward end of the outer tube 62 and in so moving has expelled the tampon 68 through the petal shaped end 66. The forward travel of the inner tube 50 will be stopped when the projection 72 engages the opposite end of the slot 56. When this occurs, the tampon 68 should be completely expelled from the outer tube 62. The applicator 60 can then be withdrawn by utilizing the finger gripping portion 64 leaving the tampon 68 in the woman's vagina. The withdrawal string 70 will remain attached to the tampon 68 so as to be available to remove the tampon 68 from the vagina.

FIGS. 14 through 17 illustrate an alternatively designed hollow tampon 80 which is composed of a body portion 82 and a withdrawal string 84. The body portion 82 has a rounded forward end 86 and a generally cylindrical central aperture or opening 88.

In FIGS. 16 and 17 hollow tampon 80 includes a cover 90 that encloses both an outer surface 92 of a wound absorbent 96 and a continuous annular surface 94 that surrounds the wall of the aperture 88. The withdrawal string 84 is securely attached to the tampon 80 by passing it around one winding 98 of the absorbent 96.

The tampons 28, 68 and 80 are stated to be formed of a wound material, but could also be formed by pressure molding a folded batt of nonwound carded material to a cylindrical shape. The tampon also does not have to be covered. The absorbents utilized in the tampon may be made from any suitable fibrous material. Typical of such materials are carded webs of polyester, rayon and cotton. The cover, if utilized, may be made from any suitable liquid permeable material such as spunbonded polypropylene or a woven gauze. The withdrawal string may be formed from cotton, rayon or polyester.

The hollow tampons 28, 68 and 80 each have an aperture which extends completely therethrough. However, a tampon could be formed with a solid rounded forward end and a hollow cavity which extends from the rear of the tampon to just short of the forward end. Such a tampon would require a somewhat longer applicator as the inner tube could not extend as far forward.

The inner tubes 14 and 50 have been illustrated as being capable of expanding radially by either using overlap windings of a sheet of resilient material or by pleating the forward end. These two methods of radial expansion are preferred as they are low in cost and can readily be formed by existing technologies. Furthermore, while radial expansion in all directions is preferred in order to obtain an even push on the tampon, the expansion could be in only one or two radial directions. The term radial expansion as used herein is intended to include expansion in less than all radial directions. It is possible that other means of radial expansion, such as an umbrella-like levered arrangement, could also be utilized. The outer tubes 12 and 62 have been shown with a narrow gripping section, although it is possible to form a simpler gripping area or to eliminate the gripping section altogether.

The materials used to form the inner and outer tubes of the applicator can be cardboard, paper or polymers such as polypropylene and polyethylene. The inner tube, if formed as a rolled sheet, should have enough resiliency to enable it to expand when withdrawn from the hollow tampon. A preferred material is polypropylene polymer for it is low in cost, flexible and easily formed. Another preferred material is paper for it is disposable as well as being low in cost. The inner tube can also be formed as a solid rod.

The embodiments of the radially expandable inner tube in combination with a hollow tampon are intended to be illustrative and not exhaustive of the possible combinations for formation of a compact tampon applicator. For instance, while the hollow tampons have been shown having cylindrical openings, the openings could be other shapes such as triangular, oval, keyhole or square. The shape of the opening can be utilized to assist in expelling the tampon after withdrawal of the inner tube. For instance, if an oval or keyhole shaped opening was present, an oval or keyhole shaped inner tube could be withdrawn and then partially turned in order to eject the tampon from the outer tube. The term radial expansion is intended to include the increase in effective diameter caused by rotation of a shaped inner tube that is not round in cross-section. Furthermore, while straight compact applicators are shown, it is possible to form curved compact applicators and arcuately shaped tampons as are disclosed in European Patent Publication No. 0 243 250 issued to Paul et al. While round crosssection applicators have been shown, the compact applicator and tampon could have an oval cross-sectional shape.

While the invention has been described in conjunction with several specific embodiments, it is to be understood that many alternatives, modifications and variations will be apparent to those skilled in the art in light of the aforegoing description. Accordingly, this invention is intended to embrace all such alternatives, modifications and variations which fall within the spirit and scope of the appended claims.

I claim:

1. A compact tampon applicator comprising:
    (a) a first member having a forward end and a rearward end with an aperture extending therebetween;
    (b) an absorbent slidably positioned in said aperture having a longitudinal opening formed therein and a withdrawal string attached to said aborbent; and
    (c) a second member having a forward end and a rearward end, said forward end being initially retained in said opening formed in said absorbent and said rearward end initially extending out of said rearward end of said first member, said second member capable of radially expanding once said forward end is removed from said absorbent and acquire a larger diameter such that it can be manually moved forward to eject said absorbent from said first member.

2. The compact tampon applicator of claim 1 wherein said first member is a hollow tube open at both ends.

3. The compact tampon applicator of claim 2 wherein said hollow tube has a plurality of petals formed about said forward end which are capable of expanding radially outward as said absorbent is ejected from said tube.

4. The compact tampon applicator of claim 3 wherein said hollow tube contains an exterior gripping surface formed adjacent to said rearward end which allows a consumer to grasp said applicator and position said forward end in her vagina.

5. The compact tampon applicator of claim 4 wherein said first member has an exterior profile consisting of two different diameters with said gripping surface being formed on the smaller diameter portion and said absorbent being retained in the larger diameter portion.

6. The compact tampon applicator of claim 1 wherein said absorbent is a cylindrically shaped tampon having a rounded forward end and said longitudinal opening extends completely through said tampon.

7. The compact tampon applicator of claim 6 wherein said withdrawal string is attached to said forward end of said tampon.

8. The compact tampon applicator of claim 1 wherein said opening formed through said absorbent is coaxially aligned with the longitudinal axis of said absorbent.

9. The compact tampon applicator of claim 8 wherein said opening has a uniform diameter.

10. The compact tampon applicator of claim 1 wherein said second member is a hollow tube formed by rolling a flat sheet.

11. The compact tampon applicator of claim 10 wherein when said hollow tube is in said initial position, it extends through said absorbent.

12. A compact tampon applicator comprising:
(a) a hollow first tube having a forward end and a rearward end;
(b) a tampon slidably positioned within said first tube, said tampon having a longitudinally aligned central aperture formed therein which is open at both ends, and a withdrawal string attached to said tampon; and
(c) a radially expandable second tube having a forward end and a rearward end, said forward end being initially retained in said central aperture and said rearward end initially extending out of said rearward end of said first tube, said second tube being capable of expanding radially once said forward end is removed from said tampon such that said second tube acquires a larger diameter and can than be manually moved forward to eject said tampon from said first tube.

13. The compact tampon applicator of claim 12 wherein said second tube has a symmetrical cross-section.

14. The compact tampon applicator of claim 12 wherein said second tube has an asymmetrical cross-section.

15. The compact tampon applicator of claim 12 wherein said first tube has a larger diameter than said second tube and has a projection formed on an inside surface thereof which cooperates with a longitudinal slot formed in said second tube to limit travel between said tubes and prevent complete withdrawal of said second tube from said first tube.

16. The compact tampon applicator of claim 15 wherein said projection engages with said slot both before and after radial expansion of said second tube.

17. The compact tampon applicator of claim 12 wherein said first member has an exterior profile consisting of two different diameters with said gripping surface being formed on the smaller diameter portion and said absorbent being retained in the larger diameter portion.

18. The compact tampon applicator of claim 17 wherein said gripping surface comprises a plurality of circular ribs.

19. The compact tampon applicator of claim 12 wherein said tampon contains a cover and has a rounded forward end.

20. The compact tampon applicator of claim 19 wherein said withdrawal string is attached to said forward end of said tampon.

21. A compact tampon applicator comprising:
(a) a hollow outer tube having a forward end and a rearward end, and having a projection formed on an inside surface of said tube;
(b) a tampon slidably positioned within said outer tube, said tampon having a longitudinally aligned central aperture formed therein which is open at both ends and a withdrawal string attached thereto; and
(c) a radially expandable inner tube having a slit formed along the entire length thereof, said inner tube having a forward end which is initially retained within said central aperture and a longitudinally aligned slot formed therein which receives said projection, said inner tube capable of radially expanding to a larger diameter once said forward end is removed from said tampon such that said inner tube can be manually moved forward to eject said tampon from said outer tube while said projection slides within said slot and prevents complete withdrawal of said inner tube from said outer tube.

22. The compact tampon applicator of claim 21 wherein said inner tube can radially expand to a diameter which is larger than the diameter of said central aperture but smaller than the outer diameter of said tampon.

23. The compact tampon applicator of claim 21 wherein said inner tube has a forward end which is fan folded in the axial direction.

24. The compact tampon applicator of claim 23 wherein said fan fold has a larger diameter than the remaining portion of said inner tube when in a contracted condition.

25. The compact tampon applicator of claim 21 wherein said projection engages with said slot both before and after radial expansion of said inner tube.

26. The compact tampon applicator of claim 21 wherein said inner tube has a forward end and a rearward end and said longitudinal slot is spaced an equal distance therebetween.

27. The compact tampon applicator of claim 26 wherein said withdrawal string is attached to a forward end of said tampon and has an unattached trailing end which passes through said inner tube and extends outward beyond said rearward end.

28. The compact tampon applicator of claim 21 wherein said tampon is formed of circularly wound layers of absorbent material and said withdrawal string is looped around at least one of said layers.

29. The compact tampon applicator of claim 21 wherein said inner tube is hollow and said longitudinal slot is located opposite to said slit formed therein.

30. A compact tampon applicator comprising:
(a) a hollow outer tube having a forward end and a rearward end and being cylindrical in shape with a rear portion which is smaller in diameter than a front portion, and having a projection formed on an inside surface of said rear portion;
(b) a tampon slidably positioned within said front portion of said outer tube, said tampon having a longitudinally aligned central aperture formed therein which is open at both ends and a withdrawal string attached thereto; and
(c) a radially expandable inner tube having a slit formed along the entire length thereof, said inner tube having a forward end which is initially retained within said central aperture and a rearward end which initially extends beyond said rearward end of said outer tube, and a longitudinally aligned slot formed therein which receives said projection, said inner tube capable of radially expanding to a larger diameter once said forward end is removed from said central aperture such that said inner tube can be manually moved forward to eject said tampon from said outer tube while said projection slides within said slot and prevents complete withdrawal of said inner tube from said outer tube.

* * * * *